United States Patent
Lim et al.

(10) Patent No.: US 7,763,028 B2
(45) Date of Patent: Jul. 27, 2010

(54) SPACER WITH HEIGHT AND ANGLE ADJUSTMENTS FOR SPACING VERTEBRAL MEMBERS

(75) Inventors: Roy Lim, Memphis, TN (US); Kevin Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 467 days.

(21) Appl. No.: 10/779,048

(22) Filed: Feb. 13, 2004

(65) Prior Publication Data

US 2005/0182416 A1 Aug. 18, 2005

(51) Int. Cl.
*A61B 17/58* (2006.01)
(52) U.S. Cl. .......................... 606/90; 606/105
(58) Field of Classification Search ............... 606/90.99, 606/105, 90, 99, 86 A, 86 B
See application file for complete search history.

(56) References Cited

U.S. PATENT DOCUMENTS

| | | | |
|---|---|---|---|
| 1,331,737 A | 2/1920 | Yilsto | |
| 5,122,130 A * | 6/1992 | Keller | ........................... 606/61 |
| 5,171,278 A | 12/1992 | Pisharodi | |
| 5,390,683 A | 2/1995 | Pisharodi | |
| 5,522,899 A | 6/1996 | Michelson | |
| 5,658,335 A | 8/1997 | Allen | |
| 5,665,122 A | 9/1997 | Kambin | |
| 5,782,832 A | 7/1998 | Larsen et al. | |
| 5,865,848 A | 2/1999 | Baker | |
| 5,888,224 A | 3/1999 | Beckers et al. | |
| 6,039,761 A | 3/2000 | Li et al. | |
| 6,045,579 A | 4/2000 | Hochshuler et al. | |
| 6,080,193 A | 6/2000 | Hochshuler et al. | |
| 6,102,950 A | 8/2000 | Vaccaro | |
| 6,126,689 A * | 10/2000 | Brett | ........................ 623/17.16 |
| 6,174,334 B1 | 1/2001 | Suddaby | |
| 6,176,882 B1 | 1/2001 | Biedermann et al. | |
| 6,179,873 B1 | 1/2001 | Zientek | |
| 6,183,517 B1 | 2/2001 | Suddaby | |
| 6,190,414 B1 | 2/2001 | Young et al. | |
| 6,193,757 B1 | 2/2001 | Foley et al. | |
| 6,217,579 B1 | 4/2001 | Koros | |
| 6,224,604 B1 * | 5/2001 | Suddaby | ........................ 606/80 |
| 6,332,895 B1 | 12/2001 | Suddaby | |
| 6,582,451 B1 * | 6/2003 | Marucci et al. | ............. 606/207 |
| 6,605,105 B1 * | 8/2003 | Cuschieri et al. | ............ 606/208 |
| 7,070,598 B2 * | 7/2006 | Lim et al. | ..................... 606/61 |
| 2003/0171813 A1 * | 9/2003 | Kiester | .................... 623/17.11 |
| 2003/0236520 A1 | 12/2003 | Lim et al. | |

FOREIGN PATENT DOCUMENTS

| | | |
|---|---|---|
| WO | WO 95/25485 | 9/1995 |
| WO | WO 97 00054 A | 1/1997 |

* cited by examiner

*Primary Examiner*—Eduardo C Robert
*Assistant Examiner*—Julianna N Harvey (57) ABSTRACT

A device having an adjustable height and angle to space vertebral members. The device includes a plurality of links that extend between a plate and a deployer. A first section of the deployer is moved to change the angle of the plurality of links and expand the height of the spacer. A second section of the deployer is moved to change the angle of the plate relative to the centerline. A method of using the spacer is also disclosed and includes positioning the spacer while in the closed orientation between the vertebral members. The spacer is then expanded to a second height. The angle of the spacer is than adjusted as necessary to space the vertebral members.

49 Claims, 7 Drawing Sheets

SPACER WITH HEIGHT AND ANGLE ADJUSTMENTS FOR SPACING VERTEBRAL MEMBERS

BACKGROUND

Various devices are used for controlling the spacing between vertebral members. These devices may be used on a temporary basis, such as during surgery when it is necessary to access the specific surfaces of the vertebral members. One technique in which this type of device may be used is during preparing the endplates of a vertebral member. The devices may also remain permanently within the patient to space the vertebral members.

It is often difficult to position the device between the vertebral members in a minimally invasive manner. A device that is small may be inserted into the patient and between the vertebral members in a minimally invasive manner. However, the small size may not be adequate to effectively space the vertebral members. A larger device may be effective to space the vertebral members, but cannot be inserted into the patient and between the vertebral members in a minimally invasive manner.

The devices may also only allow for a minimum amount of adjustability. Once placed in the patient, the devices can only be altered to a small extent. Additionally, adjusting the devices may be difficult either from an ergonomic standpoint, or from the amount of force necessary for adjustment.

SUMMARY

The present invention is directed to a spacer to space vertebral members. Both the height and the angle of the spacer may be adjusted as necessary. The device includes a spacer positioned on a distal end of a deploying device. The deploying device has an elongated shape such that the spacer can be positioned between the vertebral members, and a proximal section of the mechanism is positioned a distance away to allow a physician to manipulate the height and angle.

In one embodiment, the device includes first and second plates. A distal end of a deploying device may be positioned between the plates. First, second, and third link pairs may each comprise a first end connected to the first plate, and a second end connected to the second plate. The first link pair may be connected to a first section of the deploying device at a first connection. The second link pair may be connected to a second section of the deploying device at a second connection. The third link pair may be connected to a third section of the deploying device at a third connection. The deploying device may adjust the spacer height by moving the first section relative to the second section to adjust the spacer between open and closed orientations. Additionally, the deploying device may adjust the angle of the spacer by moving the third section relative to the second section.

DETAILED DESCRIPTION

Figure 7:
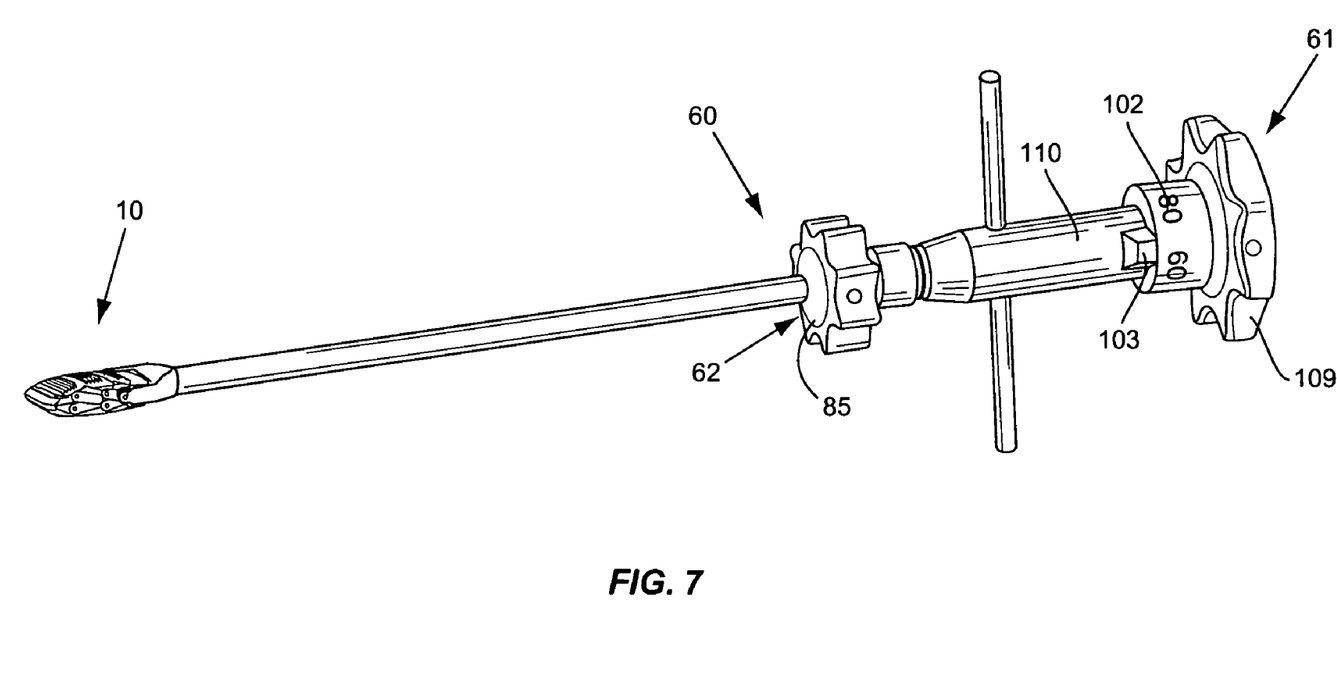
FIG. 7 is a perspective view of the spacer attached to the deploying device according to one embodiment of the present invention.

The present invention is directed to tool to space vertebral members. The tool includes a spacer 10 and a deploying device 60 as illustrated in FIG. 7. The deploying device 60 controls both the height and the angle of the spacer 10. The spacer 10 positioned on a distal end of the deploying device 60. The deploying device 60 has an elongated shape such that the spacer 10 is positioned between the vertebral members, and a proximal section of the mechanism is positioned a distance away to allow a physician to manipulate the height and angle.

Figure 2:
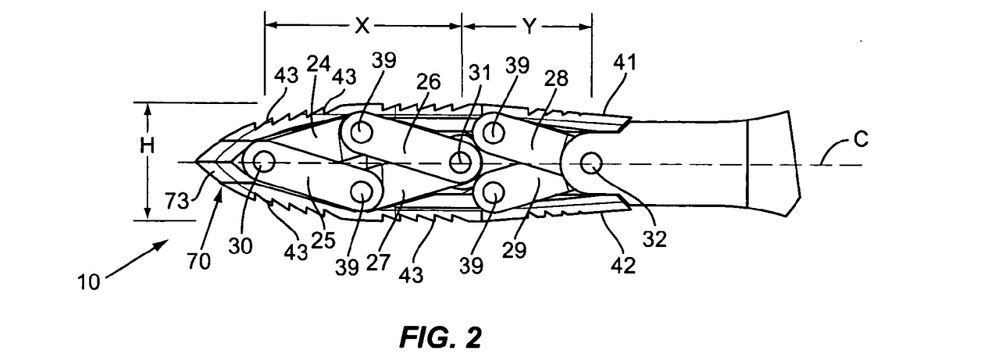
FIG. 2 is a side view illustrating the spacer in a closed orientation according to one embodiment of the present invention.
Figure 3:
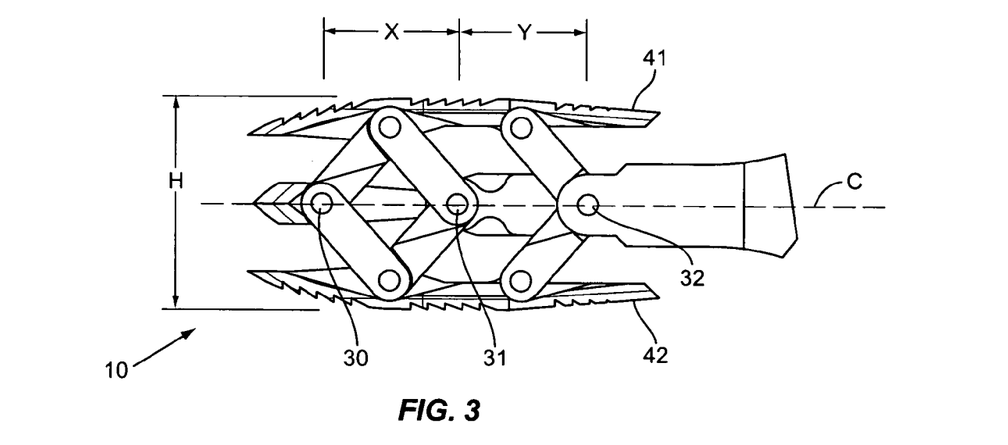
FIG. 3 is a side view illustrating the spacer in an open orientation according to one embodiment of the present invention.
Figure 4:
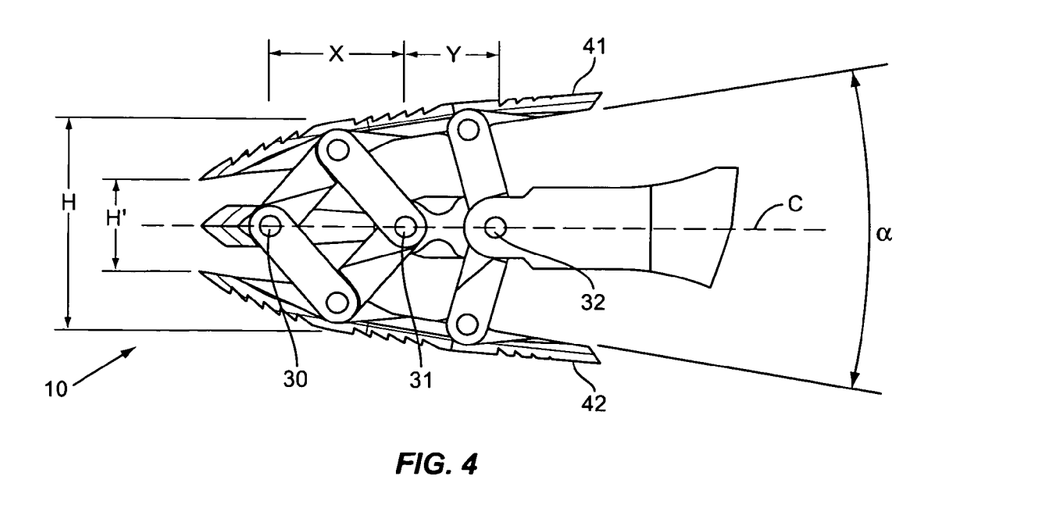
FIG. 4 is a side view illustrating the spacer in another open orientation according to one embodiment of the present invention.

The spacer 10 is selectively positionable between a closed orientation (FIG. 2) and an open orientation (FIGS. 3 and 4). The spacer 10 has an enlarged height in the open orientation defined by the distance between the upper and lower plates 41, 42. The plates 41, 42 move outward from a centerline C as the spacer 10 expands to the open position. The plates 41, 42 may also be angled relative to the centerline C to adjust for a variety of angles.

The first plate 41 and second plate 42 contact the vertebral members and form the outer surfaces of the spacer 10. As illustrated in embodiment of FIG. 2, each of the plates 41, 42 has an angled shaped towards the distal end. A nose 73 at the distal end of the first member 70 of the deploying device 60 conforms to the angled shapes giving the device a bullet shape that facilitates insertion between the vertebral members. Ridges 43 may be positioned on the plates 41, 42 to secure the device 10 in the disc space between the vertebral members.

Figure 5:
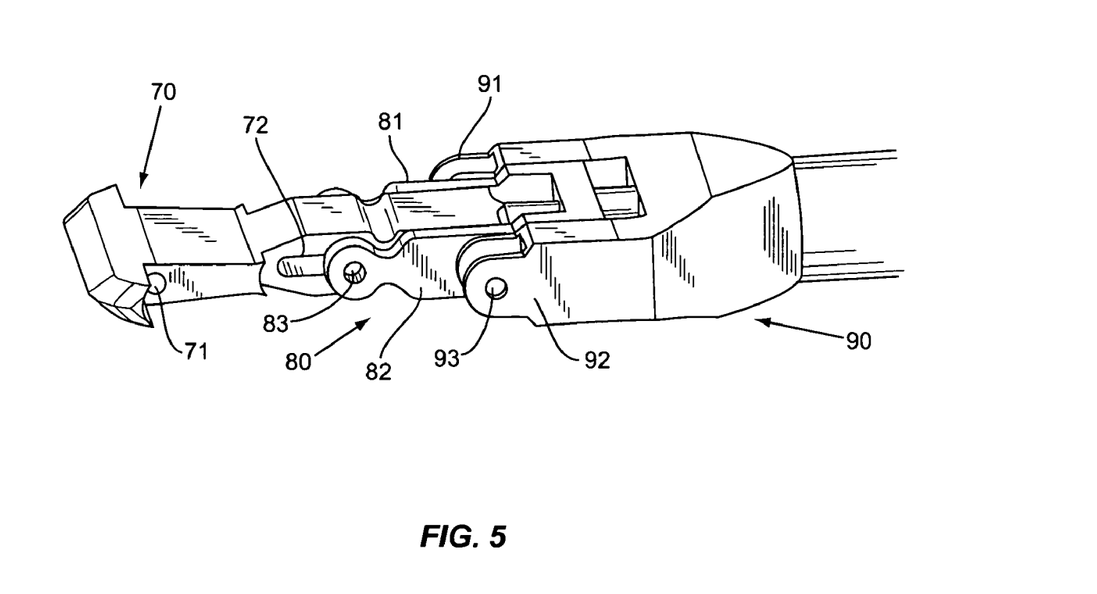
FIG. 5 is a perspective view of the distal end of the deploying device in a first orientation according to one embodiment of the present invention.
Figure 6:
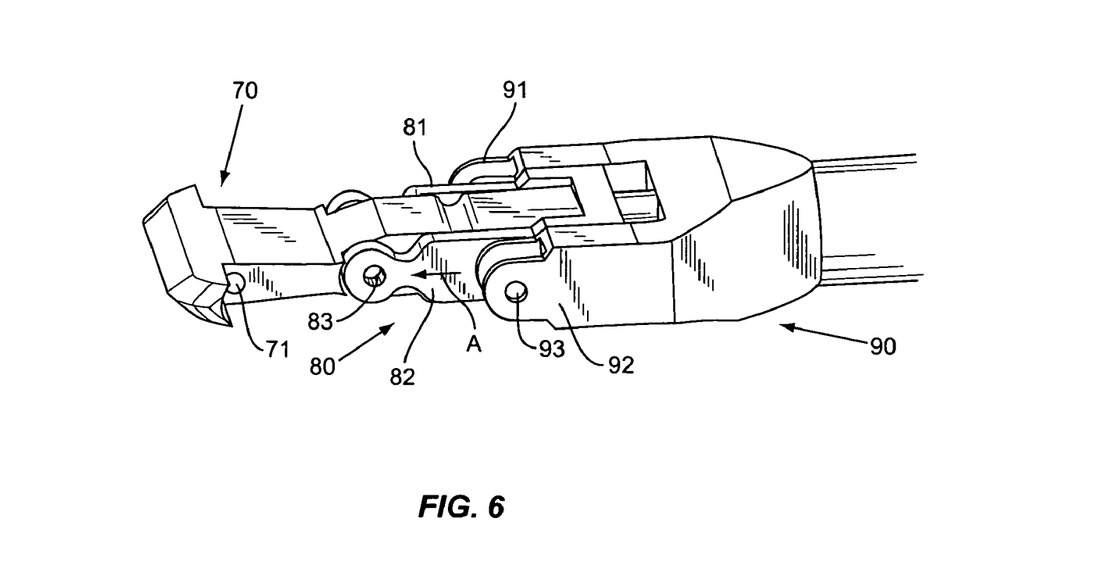
FIG. 6 is a perspective view of the distal end of the deploying device in a second orientation according to one embodiment of the present invention.

A deploying device 60 controls the positioning of the plates 41, 42. A distal end of the deploying device 60 is positioned within the plates 41, 42. As illustrated in FIGS. 5 and 6, the deploying device between the plates 41, 42 include a first member 70, a second member 80, and a third member 90. Relative movement of these members results in the deployment of the spacer 10 as will be explained in detail below. First member 70 includes a nose 73 having an angled configuration at the distal end. An aperture 71 and slot 72 are proximal to the nose. The distal end of the second member 80 includes a pair of arms 81, 82 that extend around the first member 70. Apertures 83 in each of the arms 81, 82 align with the slot 72 in the first member 70. The distal end of the third member 90 includes a first third member 91 and a second third member 92 that align on opposite sides of the second member 80. Apertures 93 are positioned towards the distal end of each third member 91, 92.

A series of links extend between the plates 41, 42 and the deploying device 60. The device includes links extending along both a first side and second side of the deploying device 60. Each side is substantially identical and only a first side will be explained in detail with the understanding that a corresponding link structure is also included on the second side. In one embodiment, each of the links has the same length.

Each of the links includes a first end attached to the deploying device 60, and a second end attached to one of the plates 41, 42. Specifically, the series of links include: link 24 extending between the first member 70 and the upper plate 41; link 25 extending between the first member 70 and the lower plate 42; link 26 extending between the second member 80 and the upper plate 41; link 27 extending between the second member 80 and the lower plate 42; link 28 extending between the third member 90 and the upper plate 41; and link 29 extending between the third member 90 and the lower plate 42.

Figure 1:
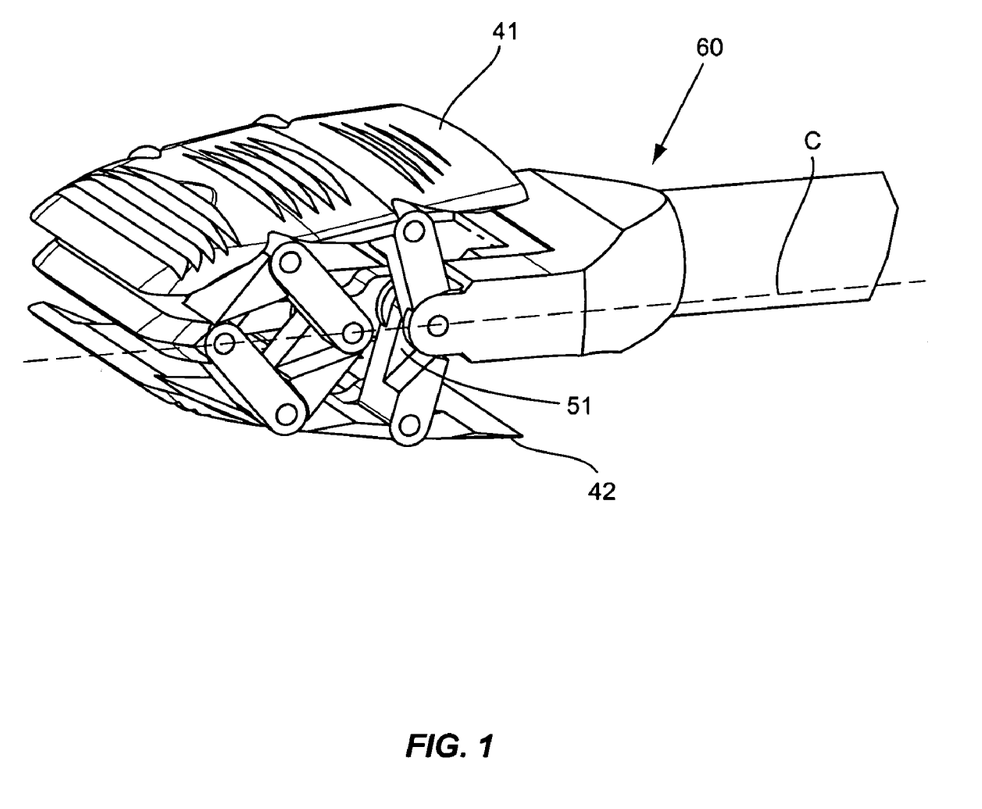
FIG. 1 is a perspective view of the spacer in an open orientation according to one embodiment of the present invention.

Each of the links is positioned in a two-pair combination that connects to the upper plate and the lower plate (i.e., link pair 24 and 25, link pair 26 and 27, link pair 28 and 29). The link pairs are constructed to overlap to conserve space and allow the plates 41, 42 to be positioned in closer proximity when the spacer 10 is in the closed orientation. In one embodiment as illustrated in FIG. 1, each link in the pair includes a complementary recessed shape 51. The recessed shapes 51 mate together in the closed orientation.

Links 24 and 26, and links 25 and 27 are operatively connected to form a linkage. Movement of one of the links of the linkage causes movement of the other link of the linkage. Embodiments of links, link pairs, and linkages are disclosed in U.S. patent application Ser. No. 10/178,960 entitled "Minimally Invasive Expanding Spacer and Method" filed Jun. 25, 2002, assigned to SDGI Holdings, Inc., the owner of the current application, and is herein incorporated by reference in its entirety.

Connection members pivotally connect the links to the plates 41, 42 and the deploying device 60. In one embodiment, a first connection member 30 extends through links 24, 25, through the aperture 71 in the first member 70, and through the corresponding links on the second side of the deploying device 60. Second connection member 31 extends through links 26, 27, apertures 83 in the second member 80, slot 72 in the first member 70, and through the corresponding links on the second side of the deploying device 60. Third connection member 32 extends through links 28, 29, and through aperture 93 in the third member 90. The third connection member 32 does not extend through the first member 70 or the second member 80. A corresponding connection member connects the two proximal links on the second side of the deploying device 60 10 to the third member 90. Additional connection members 39 connect the links to the plates 41, 42.

Deployment of the spacer 10 is caused by relative movement of members of the deploying device 60. FIG. 2 illustrates a side view of the spacer 10 in a closed orientation. In one embodiment, spacer 10 has a length of about 30 mm, a width of about 27 mm, and a height H of about 8.5 mm measured at the point of maximum convexity of the plates 41, 42. The first connection member 30 is distanced from the second connection member 31 a distance X. The second connection member 31 is distanced from the third connection member 32 a distance Y.

FIG. 3 illustrates the spacer 10 in an open orientation. The open orientation features the plates 41, 42 spaced from the centerline C. The expansion is caused by the first member 70 moving proximally relative to the second member 80 and the third member 90. The relative position of the first connection member 30 has moved relative to the second connection member 31 and the third connection member 32. This is seen as the distance X has decreased from that illustrated in FIG. 2. The distance Y between the second and third connection members 31, 32 remain the same. The force of the first member 70 moving proximally results in the links being deployed.

During the deployment, the first member 70 is proximally moved along the spacer 10. The movement results in the first connection member 30 that is positioned within aperture 71 also moving proximally. The second connection member 31 slides within the slot 72 in the first member 70 from a proximal end of the slot 72 when the spacer 10 is closed, to a distal end of the slot 72 when the spacer is deployed. This movement is illustrated in FIGS. 5 and 6 (second connection member 31 is removed in FIGS. 5 and 6 for clarity). The third connection member 32 is not connected to the first member 70 and therefore does not move. The deployment by moving the first member 70 results in the plates 41, 42 being substantially parallel during the range of deployment. The height of the spacer 10 is controlled by the amount of movement of the first member 70. In one embodiment, the height H of the spacer is about 15.4 mm measured from the points of maximum convexity of the plates 41, 42.

FIG. 4 illustrates the spacer 10 with the plates 41, 42 in the open orientation and at an angle relative to the centerline C. The angle α is the angle formed by both plates 41, 42. In one embodiment, angle α is referred to as the lordotic angle. In one embodiment, the angle α may range from about 0° to about 19°. The angle α is formed by moving the third connection member 32 relative to the second connection member 31. As illustrated in FIGS. 3 and 4, third member 90 is moved proximally causing the plates 41, 42 to form the angle α. The distance Y between the second and third connection members 31, 32 is decreased causing the proximal links 28, 29 to push outward on the proximal sections of the plates 41, 42. The relative movement between the second and third connection members 31, 32 controls the degree of the angle α. In one embodiment, the distance between the distal ends of the plates 41, 42 is about 6.7 mm.

FIGS. 5 and 6 illustrate the relative movement of the second and third members 80, 90 (third connection member 32 has been removed from FIGS. 5 and 6 for clarity). The third connection member 32 positioned within aperture 93 extends through the third member 90 without extending through the second member 80. Therefore, movement of the third member 90 does not result in movement of the second member 80. As the third member 90 moves in the direction of arrow A, the amount of angle α increases accordingly.

Figure 8:
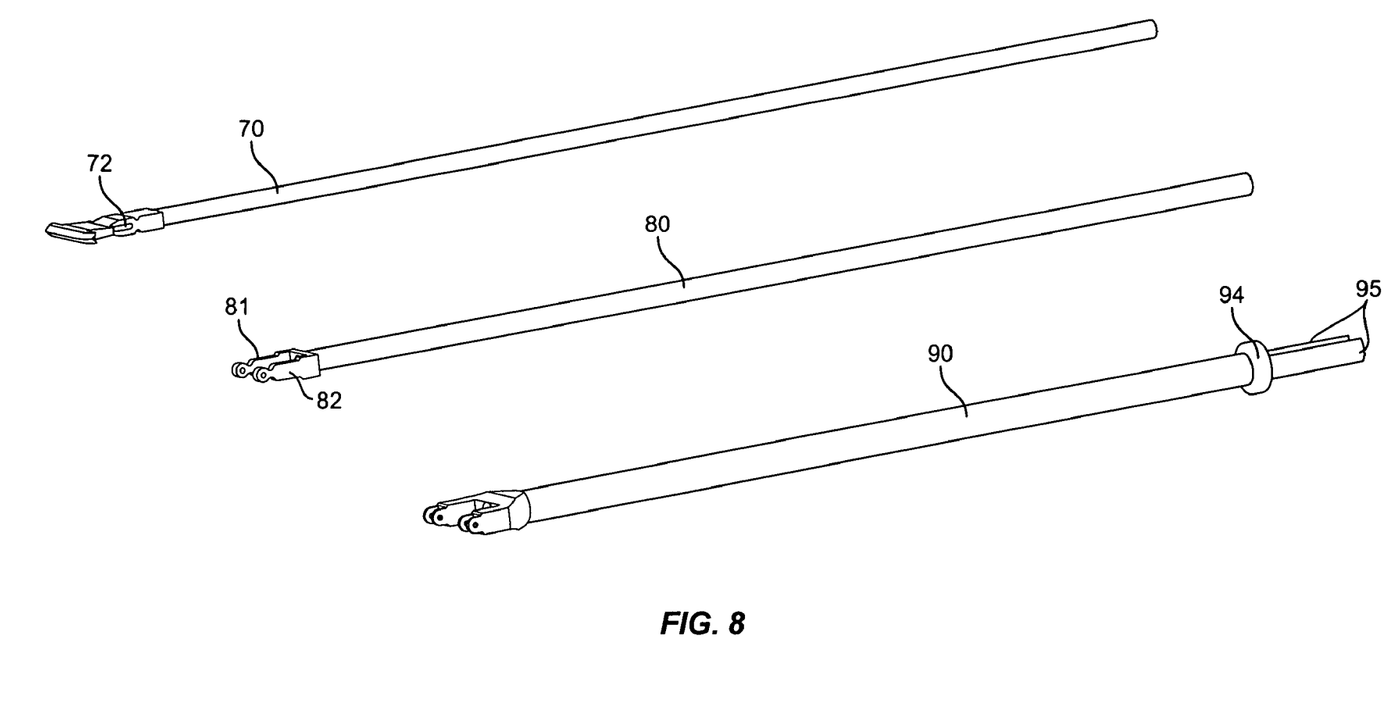
FIG. 8 is an exploded view of the first member, second member, and third member according to one embodiment of the present invention.

The deploying device 60 causes the spacer 10 to move between the open and closed orientations, and also between a variety of angles α. Deploying device 60 includes a first deploying device 61 for changing the height of the spacer 10, and a second deploying device 62 for changing the angle α. As illustrated in FIGS. 7 and 8, the proximal end of deploying device 60 is distanced from the distal end for the physician to remotely control the size and angle of the spacer 10. In one embodiment, the first member 70 includes an elongated proximal section that fits within an elongated section of the second member 80. The first member 70 is sized to move within the second member 80. The elongated section of the second member 80 with the internal proximal first member fits within the third member 90. The third member 90 is sized to move relative to the second member 80.

Figure 9:
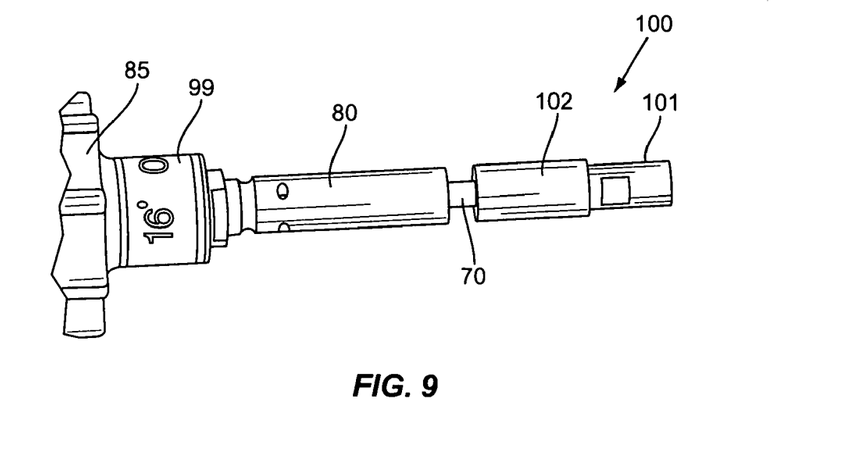
FIG. 9 is a partial side view of the proximal section of the first member and second member according to one embodiment of the present invention.

A first deploying device 61 for changing the height of the spacer 10 is illustrated in FIGS. 7 and 9. First member 70 includes a lock 100 mounted to the proximal end. Lock 100 includes a seat 101 and a sleeve 102 each having a larger cross-sectional size than a hollow interior of the second member 80. The first member 70 may be moved axially along the second member 80 between a point where the distal end of the sleeve 102 contacts the proximal end of the second member 80, and a distance where the distal sleeve end is spaced from the proximal second member end (as illustrated in FIG. 9). In one embodiment, an axial force applied to the first member 70 moves the first member relative to the second member 80. In another embodiment, the distal end of the first member 70 is threaded and mates with threads on the interior of the sleeve 102. Rotation of the sleeve 102 causes the sleeve to move along the first member 70 with the distal end of the sleeve 102 contacting and pushing the proximal end of the second member 80. Continued rotation causes the first member 70 to be pulled proximally relative to the second member 80. In both embodiments, the proximal movement of the first member 70 causes the height of the spacer 10 to increase. A force applied in the opposite direction, or rotation of the sleeve 102 in the opposite direction allows for the first member 70 to be moved distally relative to the second member 80 to reduce the height of the spacer 10.

In the rotational embodiment explained above, a knob 109 may be connected to the sleeve 102 as illustrated in FIG. 7. A gauge 102 may be positioned adjacent to the knob 101 to determine the height of the spacer 10. In one embodiment, gauge 102 includes a progressive scale that aligns with a reference point 103. The height of the spacer 10 can be determined by the position of the gauge 102 relative to the reference point 103.

Figure 10:
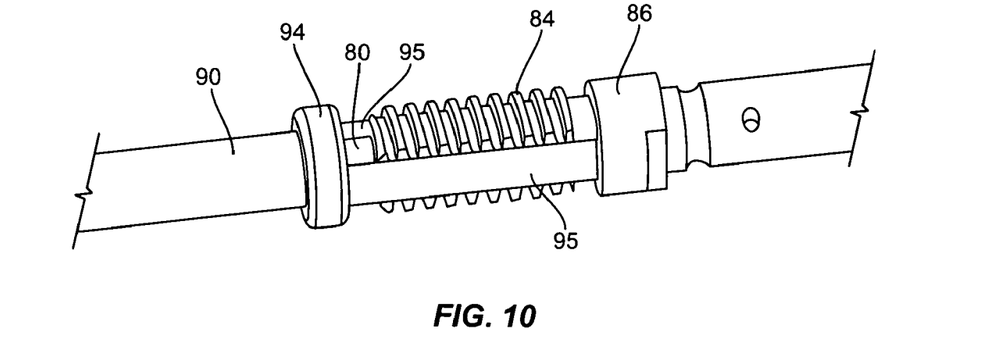
FIG. 10 is a partial side view of the proximal section of the second member and third member according to one embodiment of the present invention.

A second deploying device 62 controls the angle α. As illustrated in FIGS. 8 and 10, the proximal end of the third member 90 includes an extension 94 and a pair of spaced apart fingers 95. The proximal end of the second member 80 includes a threaded section 84 with a threaded knob 85 (FIG. 7). The knob 85 is rotated about the threaded section 84 with a distal end of the knob contacting the extension 94 to move the third member 90 in a distal direction and thus adjusting the amount of angle α. The amount of rotation of the knob 85 controls the amount of angle α. As illustrated in FIG. 9, a gauge 99 may be placed adjacent to the knob 85 to determine the amount of rotation and thus the amount of spacer angle α.

Figure 11:
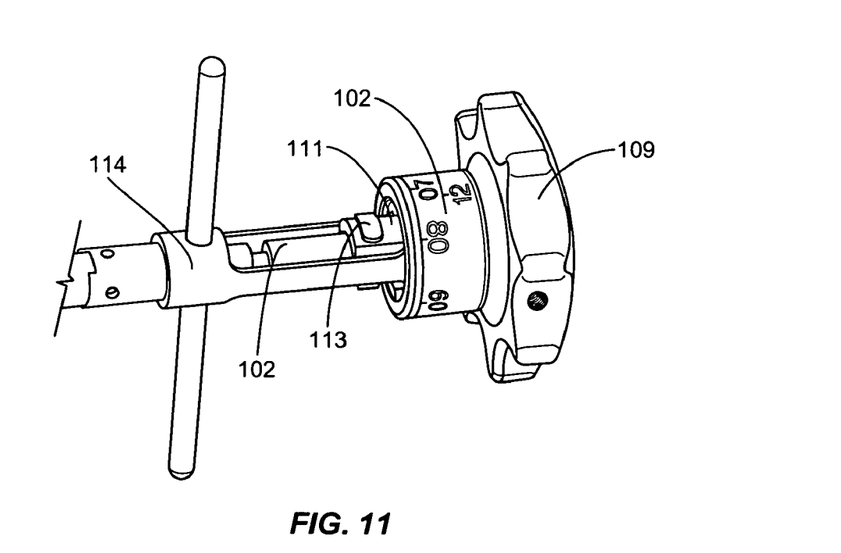
FIG. 11 is a partial perspective view of the first deploying device according to one embodiment of the present invention.
Figure 12:
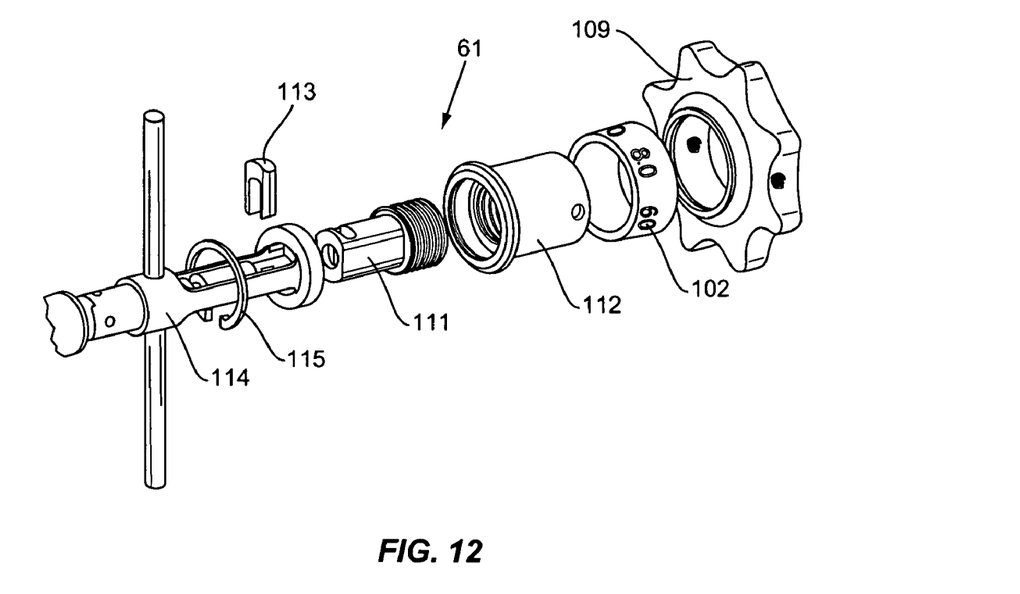
FIG. 12 is an exploded view of the first deploying device according to one embodiment of the present invention.

FIG. 7 illustrates a cover 110 extending over the proximal section of the deploying device 60. FIG. 11 illustrates the proximal section without the cover 110. FIG. 12 illustrates an exploded view of the proximal section of the first deploying device 61 that controls the spacer height. A screw 111 is connected to the seat 101 and a frame 114 is connected to the second member 80. A sleeve 112 is mated to the frame 114 and is retained by a retaining ring 115. The retaining ring 115 rotates freely about the third member 90 (not illustrated). Rotation of the knob 109 rotates the sleeve 112 and moves the screw 111 proximally. This proximal movement provides the distraction of the spacer 10. Lock 113 is inserted into an aperture in screw 111 and mates with machined flats on seat 101.

Figure 13:
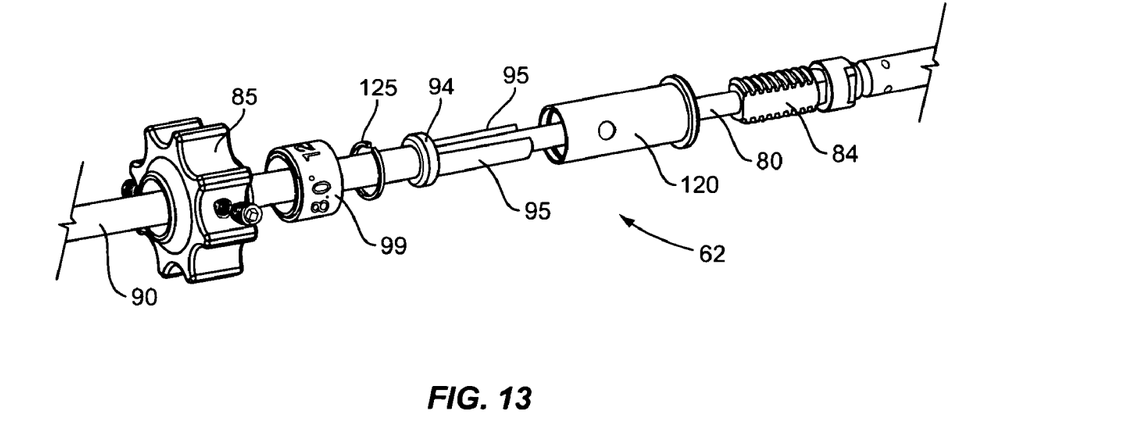
FIG. 13 is an exploded view of the second deploying device according to one embodiment of the present invention.

FIG. 13 illustrates an exploded view of the second deploying device 62. The distal end of the third member 90 includes spaced apart forks 95. The second member 80 is positioned within the third member and the threaded section 84 is positioned at a proximal end of the forks 95. A sleeve 120 extends over the fork 95 and is retained by a retaining ring 125. The retaining ring rotates freely about the third member 90. An internal thread on the sleeve 120 engages with the threaded section 84 on the second member 80. The forks 95 are machined to index with machined edges of the threaded section 84. Rotation of the knob 85 rotates the sleeve 120 that travels along the thread of the threaded section 84 and moves the third member 90 to move distally.

The arrangement of the first member 70, second member 80, and third member 90 may have a variety of configurations. In the embodiments illustrated, the first member 70 and second member 80 are nested within the third member 90. In other embodiments, the first member 70 and/or second member 80 may be positioned external to each other and the third member 90. The various arrangements should provide for relative movement of the members of the deploying device 60 to allow for changes in height and angles.

The angle α of the spacer 10 may also be negative with the proximal ends of the plates 41, 42 being in closer proximity than the distal ends. This is accomplished by moving the third connection member 32 proximally relative to the second connection member 31.

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions. In one embodiment, spacer 10 is positioned within the disc space between adjacent vertebra. Plates 50 contact the end plates of the vertebra to space the vertebra as necessary. In one embodiment, the spacer 10 is inserted posteriorly in the patient. In another embodiment, the spacer 10 is inserted from an anteriorly into the patient. In another embodiment, the spacer is inserted laterally into the patient.

In another embodiment (not illustrated), spacer 10 includes only one moving plate. A first plate moves as discussed above, and a second plate is stationary. The links move outward from the stationary plate to expand the height of the spacer 10 to the open orientation. This embodiment may include any number of links depending upon the desired spacing and strength requirements. In one embodiment, the first plate 41 expands away from the plate 42 by links 24, 26, 28.

The spacer 10 may be removable from the deploying device 60. The spacer 10 may be temporarily left between the vertebral members with the deployment mechanism removed during the procedure to provide the physician with a better view and greater work area. After the procedure, the spacer 10 may remain within the patient between the vertebral members, or the deploying device 60 may be re-engaged for spacer removal. The spacer 10 may also be returned to the closed orientation after re-engagement and prior to the spacer 10 being removed from the patient.

The present invention may be carried out in other specific ways than those herein set forth without departing from the scope and essential characteristics of the invention. In one embodiment, spacer 10 and delivery device 80 are constructed of stainless steel. In one embodiment, the distal ends of the plates 41, 42 contact in the closed orientation. The first deploying device 61 may be positioned proximal to or distal to the second deploying device 62. The present embodiments are, therefore, to be considered in all respects as illustrative and not restrictive, and all changes coming within the meaning and equivalency range of the appended claims are intended to be embraced therein.

What is claimed is:

1. A device to space vertebral members comprising:
a first plate;
a second plate;
a deploying device positioned between the first plate and the second plate;
first, second, and third link pairs each comprising a first end connected to the first plate, and a second end connected to the second plate, the first link pair connected to a first section of the deploying device at a first connection, the second link pair connected to a second section of the deploying device at a second connection, the third link pair connected to a third section of the deploying device at a third connection, and the first, second, and third connections being disposed on and spaced apart along a longitudinal axis of the device, each of the first, second, and third sections including a tubular shape and being in a telescoping arrangement with the first section positioned within the second section and the second section being positioned within the third section;
the deploying device positionable between a first orientation having a first height along a transverse axis of the device between the first and second plates, a second orientation having a second height along the transverse axis between the first and second plates that is greater than the first height, and a third orientation having an angle between the plates that is greater than in the first and second orientations, a first distance between the first connection and the second connection being smaller in the second orientation than in the first orientation, and a second distance between the third connection and the second connection being smaller in the third orientation than in the second orientation;
wherein the second distance differs in the second orientation compared to the third orientation with the first distance substantially constant in the second orientation compared to the third orientation;
the first, second, and third sections of the deploying device being movable relative to each other to independently adjust the height and the angle of the plates.

2. The device of claim 1, wherein the first link pair and the second link pair are connected to the first plate at a first common point.

3. The device of claim 2, wherein the first link pair and the second link pair are connected to the second plate at a second common point.

4. The device of claim 1, wherein a distal end of the first section includes an angled nose that complements curved surfaces of the first and second plates when the deploying device is in the first orientation.

5. The device of claim 1, wherein the second height in the second orientation is about 15 mm.

6. The device of claim 1, wherein the first, second, and third link pairs are each in an overlapping configuration in the first orientation.

7. The device of claim 1, wherein the first, second, and third link pairs are angled at a lesser amount relative to a centerline in the first orientation than in the second orientation, wherein the centerline extends along the longitudinal axis.

8. The device of claim 1, wherein each of the link pairs has an equal length.

9. The device of claim 1, wherein the third link pair is positioned proximal to the first link pair and the second link pair.

10. The device of claim 1, wherein the first connection comprises a first connection member that extends through the first link pair and the first section.

11. The device of claim 10, wherein the second connection comprises a second connection member that extends through the first section and the second section.

12. The device of claim 11, wherein the third connection comprises a third connection member that extends through the third section.

13. The device of claim 1, further comprising a slot in the second section to receive a connection member at the second connection, the connection member movable within the slot between a proximal position in the first orientation, and a distal position in the second orientation.

14. The device of claim 1, wherein the first plate and the second plate are positioned at a distal end of the deploying device, and an adjustment member is positioned at a proximal end of the deploying device to control the movement of the first section relative to the second section.

15. The device of claim 14, wherein the adjustment member comprises a rotating knob operatively connected to the deploying device to selectively position the first section relative to the second section and position the plates between the first height and the second height.

16. The device of claim 15, further comprising a second rotating knob operatively connected to the deploying device to selectively position the third section relative to the second section and control the angle between the first plate and the second plate.

17. The device of claim 16, further comprising gauges adjacent to each of the rotating knob and the second rotating knob to determine the second height and the angle.

18. A device to space vertebral members comprising:
a first plate;
a second plate;
a deploying device positioned between the first plate and the second plate;
first, second, and third link pairs each comprising a first end connected to the first plate, and a second end connected to the second plate, the first link pair connected to a first section of the deploying device at a first connection, the second link pair connected to a second section of the deploying device at a second connection, the third link pair connected to a third section of the deploying device at a third connection, and the first, second, and third connections being disposed on and spaced apart along a centerline of the device, the first, second, and third sections of the deploying device being movable relative to each other;
the deploying device positionable between a first orientation having a first height along a transverse axis of the device between the first and second plates, a second orientation having a second height along the transverse axis between the first and second plates that is greater than the first height, and a third orientation having an angle between the plates that is greater than in the first and second orientations, a first distance between the first connection and the second connection being smaller in the second orientation than in the first orientation, and a second distance between the third connection and the second connection being smaller in the third orientation than in the second orientation;
the first section, second section, and third section of the deploying device being nested together in an overlapping arrangement away from the first plate and the second plate;
wherein the first plate and the second plate are substantially parallel in the first and second orientations.

19. The device of claim 18, wherein the angle between the plates is adjustable between about 0° to about 19°.

20. A device to space vertebral members comprising:
a first plate and a second plate;
a deploying device positioned between the first and second plates, the deploying device having a first section, a second section, and a third section that are in a telescoping arrangement;
a plurality of links each extending between one of the first and second plates and the deploying device, each of the plurality of links positionable between a first orientation having a first angle relative to the deploying device, and a second orientation having a second angle relative to the deploying device with the second angle being greater than the first angle;
a first connection member connecting a first pair of the plurality of links to the first section of the deploying device;
a second connection member connecting a second pair of the plurality of links to the second section of the deploying device;
a third connection member connecting a third pair of the plurality of links to the third section of the deploying device;
wherein the first, second, and third connection members are disposed on and movable along a centerline of the device;
the first section being movable relative to the second section to move each of the plurality of links from the first angle to the second angle to adjust a height along a transverse axis of the device between the first and second plates; and
the third section being movable relative to the second section to move the third pair of the plurality of links to a third angle that is greater than the second angle to adjust an angle between the first and second plates.

21. The device of claim 20, further comprising a slot in the second section and the second connection member extending through the slot and connecting the second pair of the plurality of links to the deploying device, the second connection member positionable along the slot between a proximal position when the plurality of links are at the first angle, and a distal position when the plurality of links are at the second angle.

22. The device of claim 20, wherein each of the plurality of links has an equal length.

23. The device of claim 22, wherein the first linkage and the second linkage are distally positioned relative to the third pair of the plurality of links.

24. The device of claim 20, wherein the first pair and the second pair of the plurality of links mate together to form a first linkage positioned above the centerline and a second linkage positioned below the centerline.

25. A device to space vertebral members comprising:
a first plate and a second plate;
a first member positioned between the first and second plates;
a second tubular member positioned between the first and second plates;
a third tubular member positioned between the first and second plates;
each of the second and third tubular members including a tubular section positioned away from the first and second plates and a pair of spaced-apart arms that are positioned between the first and second plates;
first, second, and third link pairs each extending between the first and second plates, each of the link pairs having a first end connected to the first plate, and a second end connected to the second plate;
a first connection member connecting the first link pair to the first member;
a second connection member connecting the second link pair to the second tubular member; and
a third connection member connecting the third link pair to the third tubular member;
wherein the first, second, and third connection members are disposed on and spaced apart along a longitudinal axis of the device;
the first member being movable relative to the second tubular member to adjust a first distance between the first connection member and the second connection member and adjust a height along a transverse axis of the device between the first plate and the second plate;
the third tubular member being movable relative to the second tubular member to adjust a second distance between the second connection member and the third connection member to independently adjust an angle of the first plate and the second plate without adjusting the height;
the first member is positioned within the second tubular member and the second tubular member is positioned within the third tubular member.

26. The device of claim 25 wherein the first member is movable relative to the second tubular member to adjust said height between the first plate and the second plate while maintaining said first and second plates in a substantially constant relative angular orientation.

27. A device to space vertebral members comprising:
a first plate;
a second plate;
a first link pair extending between the first plate and the second plate and positionable between a first angle and a second angle;
a second link pair extending between the first plate and the second plate and positionable between the first angle and the second angle; and
a third link pair extending between the first plate and the second plate and positionable between the first angle and a third angle, with the second angle being greater than the first angle and the third angle being greater than the second angle;
wherein the device is adapted to control a distance along a transverse axis of the device between the first plate and the second plate responsive to movement of the second link pair relative to the first link pair;
wherein the device is adapted to control a device angle between the first plate and the second plate responsive to movement of the third link pair relative to the second link pair;
wherein the third link pair is capable of movement relative to the second link pair independent of movement of the first link pair relative to the second link pair; and
wherein each link pair includes a connection member and further wherein the respective connection members are disposed on and movable along a centerline of the device;
wherein the link pairs are connected to a telescoping deploying device with the first link pair connected at a first position, the second link pair connected to the deploying device at a second position that is proximal relative to the first position, and the third link pair connected to the deploying device at a third position that is proximal relative to the second position.

28. The device of claim 27, wherein a height between the first plate and the second plate is dependent on a first distance between the first position and the second position, and an angle between the first plate and the second plate is dependent on a second distance between the second position and the third position.

29. A device to space vertebral members comprising:
first, second, and third links each comprising an elongated shape with a first end and a second end;
a telescoping deploying device with three nested members, the deploying device connected to the first end of each of the first, second, and third links, the first ends being disposed on and spaced apart along a centerline of the device; and
a first plate connected to the second end of each of the first, second, and third links;
the deploying device positioned at a first orientation with the first, second, and third links at a first angle and the first plate a first distance along a transverse axis of the device from the deploying device and substantially parallel to the deploying device, at a second orientation with the first, second, and third links at a second angle greater than the first angle and the first plate at a second distance along the transverse axis from the deploying device that is greater than the first distance with the first plate being substantially parallel to the deploying device, and a third orientation with the third link at a third angle greater than the second angle and the first plate angled with the deploying device;
wherein a first distance between the first end of the second link and the first end of the third link is capable of being adjusted independently of a second distance between the first end of the first link and the first end of the second link.

30. The device of claim 29, further comprising a second plate positioned on a second side of the deploying device.

31. The device of claim 30, wherein the second plate is substantially parallel with the deploying device in the first and second orientations, and angled with the deploying device in the third orientation.

32. A method to space vertebral members comprising the steps of:
placing a spacer with a height along a transverse axis of the spacer between the vertebral members while in a closed orientation, the spacer including a pair of opposing plates and a linkage formed by a first pair of links pivotally connected together along a longitudinal axis of the spacer at a first connection point and a second pair of links pivotally connected together along the longitudinal axis of the spacer at a second connection point, the spacer also including a third pair of links pivotally connected together along the longitudinal axis of the spacer at a third connection point;
increasing the height along the transverse axis by expanding the linkage outward and decreasing a first distance along the longitudinal axis of the spacer between the first and second connection points;
changing an angle of the spacer by decreasing a second distance between the second and third connection points; and
maintaining the first, second, and third connection points spaced apart along the longitudinal axis of the spacer while increasing the height and changing the angle of the spacer.

33. The method of claim 32, wherein the step of changing the angle of the spacer comprises adjusting the angle between about 0° and about 19°.

34. The method of claim 33, wherein the step of increasing the height comprises changing the height from about 8 mm to about 15 mm.

35. The method of claim 32 wherein the step of increasing the height along the transverse axis further comprises increasing a height between a first plate and a second plate, the first and second plates disposed on opposite sides of the transverse axis.

36. The method of claim 35 wherein the step of increasing the height between the first and second plates further comprises maintaining a central portion of the linkage and a link of the third pair of links mounted to the first plate and spaced apart a constant amount.

37. The method of claim 32 wherein the step of changing the angle of the spacer by decreasing the second distance between the second and third connection points comprises decreasing the second distance while simultaneously maintaining the first distance substantially constant.

38. A method to space vertebral members comprising the steps of:
placing a spacer with a height along a transverse axis of the spacer between the vertebral members while in a closed orientation;
increasing the height along the transverse axis by expanding a linkage outward by moving a first section of a deploying device along a longitudinal axis of the spacer proximally relative to a second section also on the longitudinal axis of the spacer and decreasing a first distance measured along the longitudinal axis of the spacer between a first linkage end and a second linkage end;
changing an angle of the spacer while simultaneously maintaining the first distance substantially constant by moving a third section of the deploying device along the longitudinal axis of the spacer relative to the second section and decreasing a second distance measured along the longitudinal axis of the spacer between a first link end and the second linkage end and driving a second link end outward from the deploying device; and
continuously maintaining the first linkage end, the second linkage end, and the first link end disposed on and spaced apart along the longitudinal axis of the spacer.

39. The method of claim 38, wherein the step of increasing the height by expanding the linkage outward by moving the first section of the deploying device proximally relative to the second section further causes the second link end to move outward from the deploying device.

40. The method of claim 39, wherein the step of increasing the height by expanding the linkage outward by moving the first section of the deploying device proximally relative to the second section causes the second distance to remain unchanged.

41. The method of claim 38, further comprising rotating a knob on a proximal section of the deploying device and moving the first section relative to the second section.

42. The method of claim 41, further comprising rotating a second knob on the proximal section of the deploying device and moving the third section relative to the second section.

43. The method of claim 38 wherein the step of increasing the height along the transverse axis further comprises increasing a height between a first plate and a second plate, the first and second plates disposed on opposite sides of the transverse axis.

44. The method of claim 43 wherein the step of increasing the height between the first and second plates further comprises maintaining a central portion of the linkage and the second link end mounted to the first plate and spaced apart a constant amount.

45. The method of claim 38 wherein the step of changing the angle of the spacer by moving the third section of the deploying device relative to the second section and decreasing the second distance between the first link end and the second linkage end and driving the second link end outward further comprises decreasing the second distance while simultaneously maintaining the first distance substantially constant.

46. A method to space vertebral members comprising:

positioning a spacer with a height along a transverse axis of the spacer in a closed orientation between the vertebral members;

moving a first section of a deploying device proximally relative to a second section of the deploying device and moving a first link pair closer to a second link pair, increasing a first link pair angle, and moving a plate away from a centerline extending along a longitudinal axis of the spacer; and moving a third section of the deploying device distally relative to the first and second sections of the deploying device and moving a third link pair closer to the second link pair, increasing a third link angle relative to the centerline, and increasing an angle of the plate relative to the centerline; and maintaining a first connection between the first link pair and the first section of the deploying device, a second connection between the second link pair and the second section of the deploying device, and a third connection between a third link pair and the third section of the deploying device disposed on and spaced apart along the centerline.

47. The method of claim 46 wherein the step of moving the plate away from the centerline extending along the longitudinal axis of the spacer further comprises moving a second plate away from the centerline, the plate and the second plate disposed on opposite sides of the centerline.

48. The method of claim 47 wherein the step of moving the plate away from the centerline further comprises maintaining a fourth connection between the first and second link pair and the plate and a fifth connection between the third link pair and the plate mounted to the plate and spaced apart a constant amount.

49. The method of claim 46 wherein the step of moving the third link pair closer to the second link pair further comprises moving the third link pair closer to the second link pair while simultaneously maintaining a distance between the first link pair and the second link pair substantially constant.

* * * * *